United States Patent [19]

Cohen et al.

[11] 4,080,264

[45] Mar. 21, 1978

[54] IMMUNOASSAY BY LIGHT SCATTERING SPECTROSCOPY

[75] Inventors: Richard J. Cohen, Cambridge; George B. Benedek, Belmont, both of Mass.

[73] Assignee: Massachusetts Institute of Technology, Cambridge, Mass.

[21] Appl. No.: 662,497

[22] Filed: Mar. 1, 1976

[51] Int. Cl.² ............................................. G01N 31/00
[52] U.S. Cl. ...................... 195/103.5 A; 195/103.5 R; 195/103.5 V; 356/103; 424/12
[58] Field of Search ................. 195/103.5 A, 103.5 R, 195/103.5 V; 424/12; 356/102, 103, 104

[56] References Cited

U.S. PATENT DOCUMENTS

| | | | |
|---|---|---|---|
| 3,905,767 | 9/1975 | Morris et al. ................. | 195/103.5 A |
| 3,967,901 | 7/1976 | Rodriguez ............................ | 356/103 |
| 3,984,533 | 10/1976 | Uzgiris .................................... | 424/12 |
| 3,990,851 | 11/1976 | Gross et al. ............................ | 424/12 |

*Primary Examiner*—Lionel M. Shapiro
*Assistant Examiner*—C. A. Fan

*Attorney, Agent, or Firm*—Arthur A. Smith, Jr.; Robert Shaw; Paul J. Cook

[57] ABSTRACT

This inventin provides a means for determining the concentration of any of a wide range of antibody or antigen molecules with a high degree of specificity, accuracy and sensitivity. Antigen or antibody concentration is determined by effecting an agglutination reaction in a liquid medium and determining the mean diffusion constant of the agglutinated reaction product by quasi-elastic light scattering spectroscopy. The measured mean diffusion constant then is compared with a standard quantitative relationship between mean diffusion constant and concentration of the antigen or antibody being tested. By this means one may specifically ascertain the absolute concentration of the antigen or antibody in question in the sample being analyzed. In addition to detecting antigen or antibody molecules, the process of this invention can be used to determine the concentration of any substance capable of specifically promoting or inhibiting an agglutination reaction such as viruses, white blood cells or the like.

16 Claims, 1 Drawing Figure

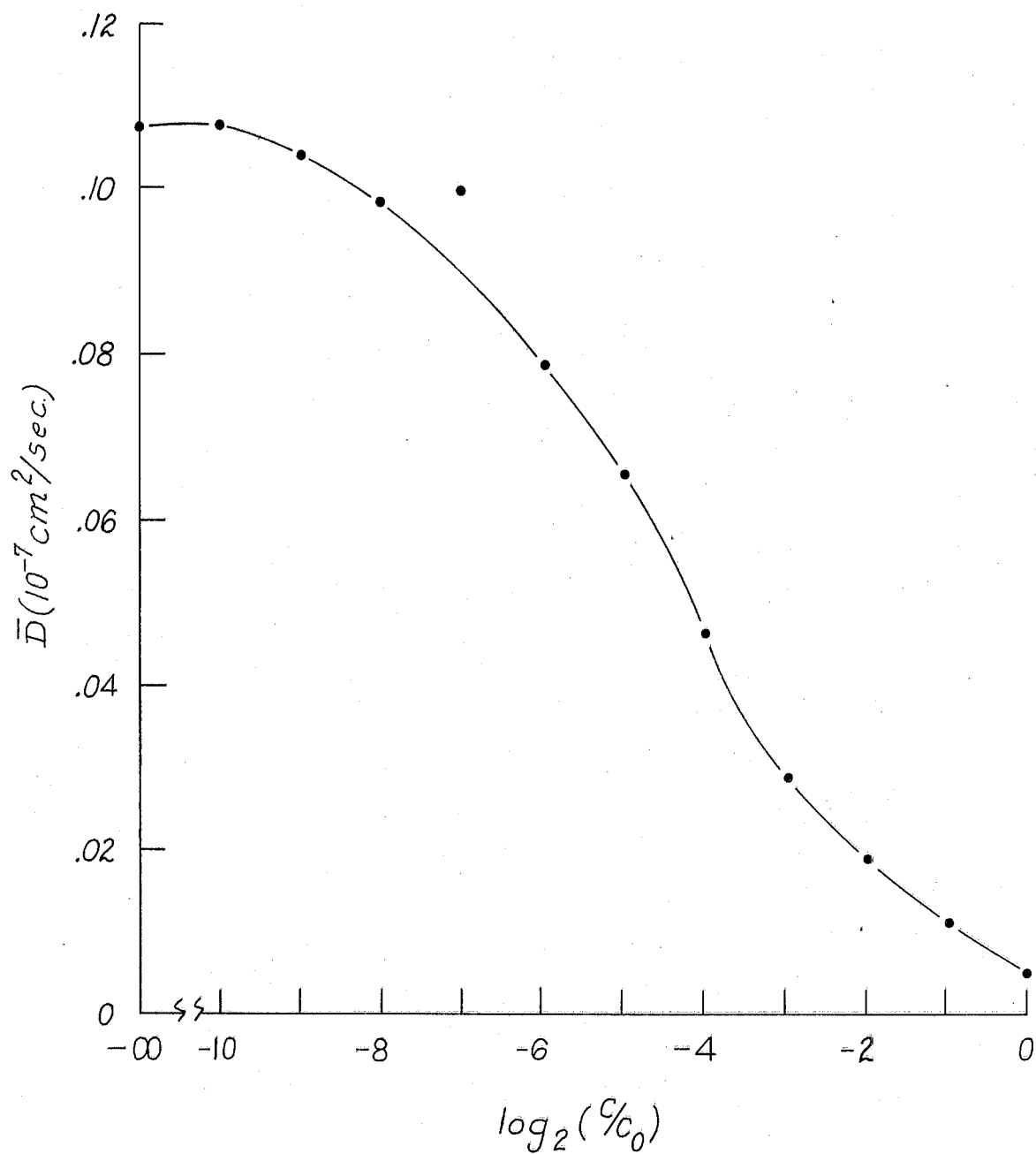
Mean diffusion constant $\bar{D}$ vs $\log_2 (C/C_0)$ where $C$ is the antibody concentration and $C_0 = 5$ µg antibody/ml

IMMUNOASSAY BY LIGHT SCATTERING SPECTROSCOPY

The Government has rights in this invention pursuant to Grant No. 5-P01 HL14322-03 awarded by the National Institute of Health.

BACKGROUND OF THE INVENTION

This invention relates to a process for determining the concentration of substances capable of promoting or inhibiting agglutination reactions and measuring the degree of reaction by quasi-elastic light scattering spectroscopy.

Agglutination reactions are widely used in biology and medicine to detect small quantities of antibody or antigen molecules. Agglutination reactions usually involve the in vitro aggregation of microscopic carrier particles which bear on their surface antigenic molecules. Aggregation occurs when antibody molecules specifically corresponding to the antigen are introduced into the solution of the carrier particles. The converse procedure of agglutinating antibody-coated particles with the appropriate polyhaptenic antigen molecules is also used. Some of the carrier particles which have been used are red blood cells, bacteria and polystyrene spheres. At low concentrations of the agglutination-inducing antibody or antigen (henceforth termed the agglutinator), small aggregates consisting of only a few carrier particles are formed. At higher concentrations of agglutinator the aggregates grow so large as to form visible clumps.

Conventionally, the appearance of this visible agglutinate has been taken as the criterion for the presence of the agglutinator. Clearly this detection criterion suffers from several defects. First, the formation of the grossly visible agglutinate requires a much larger concentration of agglutinator than needed to form small microscopic aggregates. Moreover, whereas the reversible formation of small aggregates is a specific and reproducible process, the appearance of macroscopic agglutinates is subject to many poorly controlled influences, such as the presence of foreign surfaces. In addition, the appearance of a grossly visible agglutinate is so qualitative a criterion that it is difficult experimentally to determine quantitatively the associated agglutinator concentration. Conventionally, the agglutinator concentration is determined by preparing a serial dilution of the agglutinator-containing solution. Then an aliquot of each dilution is mixed with a fixed amount of carrier particles (henceforth all the reagents, including carrier particles, used in fixed amount will be collectively termed the agglutinant) and the highest degree of dilution which still permits the formation of a visible agglutinate, is noted. This serves to indicate the concentration of agglutinator in the original solution. The agglutinator concentration can at best be determined to within a factor of two by this method.

Thus while the agglutination reaction, as conventionally performed serves as a specific and versatile means of detecting antigen or antibody molecules, it is severely limited in its application in that: (1) the process is not capable of providing an accurate quantitative measurement of either antigen or antibody concentrations and (2) the process may only be used for determining antibody or antigen concentrations which are sufficiently high so as to induce (or inhibit) macroscopically visible agglutination.

A present available alternative method for determining antigen concentration is the radioimmuno assay. In this method, a sample containing an unknown concentration of antigen is mixed with a fixed amount of antibody and a fixed amount of the antigen which has been radioactively labeled, usually with radioactive iodine. The resultant precipitate is recovered and its radioactivity is measured to determine the relative concentrations of the radioactive antigen and unknown antigen thereby to determine the concentration of the unknown antigen.

While this method is more sensitive than the method for visually determining agglutination reaction precipitate, it has many disadvantages. The radioimmuno assay requires the covalent linkage of a radio-isotope label to the species of antigen being measured. It is not always possible to attach this label to the desired class of molecules, and moreover the labelling process itself may distort the antigenic properties of the molecule so as to impair the sensitivity and specificity of the technique. In addition, the labelling process presents a radiation hazard and requires expensive shielding. Moreover, the labelled compounds are unstable and must be frequently prepared. Therefore, as a practical matter the use of radio-isotopes is so expensive, difficult and hazardous that in many applications the radioimmuno assay may not be used. In addition, the radioimmuno assay is not generally suitable for the measurement of antibody concentrations, and thus is undesirably limited to determining antigen concentrations.

In addition to determining antigen and antibody concentrations, the process of this invention can be used to determine the concentration of any substance capable of specifically promoting or inhibiting an agglutination reaction even where the formation of antigen-antibody bonds may not be involved in the agglutination process. For example, certain viruses are able to directly agglutinate red blood cells. Also, certain types of white blood cells of one individual may be able to agglutinate cells of another individual. The concentration of such viruses or white blood cells can be determined by effecting the appropriate agglutination reaction and determining the degree of reaction by quasi-elastic light scattering spectroscopy.

SUMMARY OF THE INVENTION

This invention provides a means for specifically and quantitatively determining antigen or antibody concentration. The antigen or antibody is used to effect or inhibit an agglutination reaction in a liquid medium. The degree of agglutination is determined by measuring the mean diffusion constant $\bar{D}$ of the agglutinated reaction product by means of quasi-elastic light scattering spectroscopy. The measured diffusion constant then is compared with a standard quantitative relationship between the mean diffusion constant of the agglutinated reaction product and the concentration of antigen or antibody being tested. In addition to determining the concentration of antigen or antibody molecules, the process of this invention can be used to determine the concentration of any substance capable of specifically promoting or inhibiting an agglutination reaction even when the formation of antigen-antibody bonds is not involved in the agglutination process.

DESCRIPTION OF SPECIFIC EMBODIMENTS

Quasi-elastic light scattering spectroscopy is a laser technique used to study the Brownian motion of particles in solution. The Brownian motion of a particle in solution is characterized by its diffusion constant D, which is a monotonically decreasing function of particle size. This Brownian motion broadens the spectral linewidth of the laser light scattered by the particle in direct proportion to D. The spectrum (or its Fourier transform, the correlation function) of the light scattered from a polydisperse solution of particles is determined by the distribution of diffusion constants of the particles. By analysis of the spectrum (or correlation function), we may obtain $\overline{D}$ which is the average of the diffusion constants of the particles weighted by the intensity of the light scattered by each particle. The mean diffusion constant $\overline{D}$ is inversely proportional to the mean hydrodynamic radius of the particles. The appearance of even a few aggregates in a previously monodisperse solution of particles causes a marked drop in $\overline{D}$ because the aggregates scatter light more strongly than do the single particles. The scattered light is measured at a constant angle to the path of incident light. Quasi-elastic light scattering is a particularly suitable means of following agglutination in that it measures only the relative distribution of particle sizes, and is independent of absolute particle concentration. Hence, quasi-elastic light scattering measurements are insensitive to the anomalies of precipitation and absorption of particles onto foreign surfaces.

In the process of this invention, an agglutination reaction is performed in any of the modes of operation described below. The agglutination reaction may be used in several different modes to detect antigen or antibody including procedures which utilize carrier particles as follows:

(1) With antigen-coated carrier particles as agglutinant and the complementary antibody as agglutinator.

(2) With antibody-coated carrier particles as agglutinant and the complementary antigen as agglutinator.

(3) The agglutination inhibition mode with antigen-coated spheres wherein a fixed quantity of antibody is mixed with a dilution of the test sample containing the complementary antigen, inactivating a portion of the antibody. This mixture then is combined with the antigen-coated carrier particles. The degree to which the antigen in the test sample inhibits the aggregation of the carrier particles, that would otherwise have occurred, indicates the concentration of antigen present.

(4) The agglutination inhibition mode with antibody-coated spheres wherein a fixed quantity of antigen is mixed with a dilution of the test sample containing the complementary antibody, inactivating a portion of the antigen. This mixture then is combined with the antibody-coated carrier particles. The degree to which the antibody present in the sample inhibits the aggregation of carrier particles, which would otherwise have occurred, indicates the concentration of antibody present.

In modes 1 and 4 the agglutination reaction serves as an antibody assay. In modes 2 and 3 it serves as an antigen assay. Mode 3 is of particular practical importance as an antigen assay since it is generally easier to obtain a sufficient quantity of purified antigen to coat the carrier particles than to obtain a similar quantity of complementary antibody. Moreover, in mode 3 the agglutination reaction serves to detect antigen molecules of any size with one or more haptenic sites. On the other hand, in mode 1 the agglutination reaction serves to detect only polyhaptenic antigens, which are of sufficient size (on the order of 100 A in diameter) to effect crosslinking of the carrier particles.

A standard quantitative relationship first is established between the mean diffusion constant $\overline{D}$ of the agglutinated reaction product as a function of the concentration of the antigen or antibody being tested for fixed concentrations of the agglutinant composition. Antigen or antibody-coated particles can be prepared by depositing the antigen or antibody on the surface of latex microspheres, red blood cells, bacteria or the like by means well known in the art. In addition some cells or bacteria naturally bear certain antigens or antibodies on their surface. Serial dilutions of known concentration of the antigen or antibody one wishes to test then are prepared and an agglutination reaction is performed using these serial dilutions of known concentration of antigen or antibody with the fixed concentrations of the agglutinant composition. The concentration of agglutinator present must be sufficiently low so that precipitation of the agglutinated particles does not occur, so that the agglutinated particles remain suspended in solution. The agglutination reaction involves the cross-linking of the coated particles to produce larger particles in proportion to the concentration of active agglutinator present. This cross-linking has the effect of reducing the mean diffusion constant measured by quasi-elastic light scattering spectroscopy in proportion to the concentration of active agglutinator present. For each serial dilution of the known concentration of antigen or antibody tested, the value of $\overline{D}$ is determined for the corresponding agglutinated reaction product by means of quasi-elastic light scattering spectroscopy as described above.

The quantitative relationship so-determined then can be employed as a standard to be applied when performing the agglutination reaction on samples containing unknown amounts of the antigen or antibody being tested. A serial dilution of each sample is prepared. The agglutination reaction is performed using one or several of these dilutions of the sample and the means diffusion constant $\overline{D}$ is determined. The agglutinant composition employed to establish the standard quantitative relationship must be the same agglutinant composition employed to form the agglutinated reaction product with the antigen or antibody being tested so that an accurate comparison can be made between the standard and the unknown. The measurements of $\overline{D}$ of the agglutinated reaction product obtained with the antigen or antibody being tested are compared with the standard quantitative relationship between $\overline{D}$ and the antigen or antibody concentration, and thus the original concentration of the antigen or antibody in the sample is determined. At least two sample dilutions should be analyzed by light scattering spectroscopy in order to extrapolate the results to the standard quantitative relationship. However, only one sample dilution is needed if it is known that, at the concentration tested, it is within an ascending of descending portion of the relationship between concentration and mean diffusion constant.

It is also possible to use the process of this invention to measure the concentration of antigen or antibody without the use of carrier particles. Thus, in addition to the modes of operation set forth above, the concentration of antigen is determined by mixing a fixed amount of complmentary antibody to the serial dilutions of the sample which contains the antigen (mode 5). Quasi-elastic light scattering then is used to measure $\overline{D}$ of the reaction product and this is compared with standard quantitative relationship. The larger the antigen-antibody aggregates the smaller is $\overline{D}$. In mode 6 of the method of this invention antibody concentration is determined by mixing a fixed amount of complementary antigen with the serial dilutions of the sample containing the antibody. Once again $\overline{D}$ of the reaction product is measured and is compared with a standard quantitative relationship. In practice, the process of this invention is more sensitive in modes 1, 2, 3, 4 where carrier particles are utilized as compared to modes 5 and 6. Also, there is less interference in the measurement of $\overline{D}$ due to light scattered by other elements present in the sample in modes 1,2,3,4 as compared to modes 5 and 6 since the intensity of light scattered by the large carrier particles is generally much greater than that scattered by any other element. However modes 5 and 6 are useful when it is not possible to bind the antigen or antibody to a suitable carrier particle.

The process of this invention provides substantial advantages over the processes of the prior art. Since the process does not require that the agglutination reaction be conducted at such a high concentration of agglutinator that macroscopic precipitation of the agglutination reaction product, the method of this invention can be used to measure much lower antigen or antibody concentrations associated with the microscopic reversible stages of the agglutination reaction. This stage may involve the dimerizing of the carrier particles whereas the macroscopically visible agglutinate may contain hundreds of thousands of carrier particles. In the example discussed below no macroscopic agglutinate occurred at antibody concentration as high as $5\mu g/ml$, whereas the process of this invention can detect as little as $0.01\mu g/ml$, or $10^{-13}$ moles/ml, of antibody. Moreover, in the process of this invention the agglutination reaction may be performed in volumes as small as one microliter. Thus the absolute amount of antigen or antibody detectable is on the order of $10^{-16}$ moles or about $10^7$ molecules. Moreover, in the process of this invention the degree of agglutination is quantitatively measured at the microscopic, reversible and reproducible stage of the agglutination reaction. Thus this process serves to transform the agglutination reaction from a rough qualitative measure of antigen or antibody concentration to an accurate, reproducible means of quantitating antibody or antigen concentration.

Since the process of this invention does not employ the covalent linkage of a radio-isotopic label, to the species being measured, it provides substantial advantages over the radioimmuno assay procedure described above. In addition, the process of this invention can be conducted in a matter of hours rather than days as required for radioimmuno assay.

The process of this invention is applicable for accurately determining the concentration of any antigen or antibody capable of promoting or inhibiting an agglutination reaction. Representative suitable antigens or antibodies that can be tested include hormones such as human chorionic gonadotropin which can be detected accurately to concentrations as low as about 0.016 International Units with rabbit antiserum in mode 3, luteinizing hormones, insulin, parathyroid hormone; drugs such as digoxin, barbiturates and diphenylhydantoin; and tumor and virus associated antigens or antibodies including Hepatitis-associated antigen and Carcino-Embryonic antigen. Thus the process of this invention provides a means for measuring a very wide range of antigens and antibodies of research and clinical importance. For example, the process of this invention provides an extremely accurate means for testing for stimulation of ovulation (luteinizing hormone) and for normal and ectopic pregnancy (human chorionic gonadotropin).

In addition to determining the concentration of antigen or antibody molecules, the process of this invention can be used to determine the concentration of any substance capable of specifically inhibiting or promoting an agglutination reaction even where the formation of antigen-antibody bonds is not involved in the agglutination process. In this mode of operation of the invention a fixed amount of agglutinant (the agglutinant, as before, refers to all the reagents used in fixed amount) is mixed with the serial dilutions of the test sample containing the substance being tested. The value of the mean diffusion constant of the agglutinated reaction product is determined by means of quasi-elastic light scattering spectroscopy. The mean diffusion constant so obtained is compared with the previously determined standard quantitative relationship between the mean diffusion constant of the agglutinated reaction product and the concentration of substance being measured. In such manner one may determine the concentration of viruses capable of agglutinating red blood cells. One similarly may detect the presence of white blood cells (lymphocyte cells) capable of agglutinating such cells obtained from another individual.

One may also test for the presence of antibody to any substance capable of promoting or inhibiting an agglutination reaction. In this mode of operation, a dilution of the test sample containing the antibody being tested is first mixed with a fixed amount of the substance in question (e.g. virus). This antibody inactivates a portion of the substance. The resultant mixture is combined with a fixed concentration of the particles (e.g. red blood cells) to be agglutinated by the substance. The mean diffusion constant of the agglutinated reaction product is compared with the previously determined standard quantitative relationship between the mean diffusion constant and the antibody concentration. In this manner one may determine the concentration of antibodies to particular viruses capable of inducing agglutination of red blood cells.

Inasmuch as quasi-elastic light scattering spectroscopy is capable of quantitatively detecting a much lesser degree of agglutination than previously possible, the process of this invention is capable of quantitatively detecting lower concentrations of any substance capable of promoting or inhibiting agglutination reactions as well as antibodies to such substances.

The following example illustrates the present invention and is not intended to limit the same.

EXAMPLE I

This example illustrates the process of this invention for accurately determining the concentration of antibody to bovine serum albumin (BSA).

Polystyrene spheres (0.357 $\mu m$ dia) obtained from Dow Chemical Company were dialyzed for 48 hours against distilled water to remove surfactant. A solution 1% in polystyrene spheres and 3 mg/ml in BSA was made up in 0.02 M pH 8.0 sodium phosphate buffer. This solution was allowed to incubate overnight at 4° C. In order to remove BSA molecules that had not adhered to the polystyrene spheres, the solution was centrifuged at 15,000 rev/min for 40 min., the supernatant was discarded, and the pellet resuspended in buffer. This centrifugation procedure was then repeated. The concentration of the resultant polystyrene BSA stock solution was determined by weighing the solid residue obtained by drying a measured volume of solution.

The data for FIG. 1 to establish a standard quantitative relationship between the mean diffusion constant and the antibody concentration was obtained in the following manner. Serial dilutions of rabbit antiserum to BSA obtained from Calbiochem Company were prepared in a series of test tubes. To each tube were added identical aliquots of a fixed dilution of the polystyrene-BSA stock solution prefiltered through a 1 $\mu$m Nuclepore filter. The final fluid volume per tube was 2 ml. and the final polystyrene-BSA concentration in each tube was chosen to come out to 11 $\mu$g/ml. The mixtures were allowed to incubate at room temperature for 24 hr. Then the samples were filtered through a 3 $\mu$m Nuclepore filter into a light scattering cell. Light scattering measurements were performed at 25° C and at a scattering angle of 90°. A Spectra Physics argon-ion laser run at 10mW output was used in conjunction with a double-scaled autocorrelator. Data were analyzed by the method of cumulants. Absolute antibody concentration was determined by quantitative precipitin analysis by Calbiochem Company.

As shown in FIG. 1, the aggragation can be clearly detected when the concentration of antibody is between 0.01 $\mu$g/ml and 0.02 $\mu$g/ml. This is to be compared with a minimum detectable antibody concentration of greater than 5 $\mu$g/ml that we found to be required for the appearance of a visible agglutinate in our system.

We also performed two control experiments. In one experiment we prepared serial dilutions of rabbit antiserum to BSA and added polystyrene spheres coated with horse hemoglobin. In the second experiment we prepared serial dilutions of normal rabbit serum and added polystyrene spheres coated with BSA. We compared the results of light scattering measurements made on the two control systems with the data obtained from a third identically prepared polystyrene-BSA, antiserum to BSA system. We found that in both control systems that there was no detectable agglutination until the concentration of serum was increased to a level $2^5 - 2^6$ times greater than that which the specific antigen-antibody agglutination could first be observed in our third system. The nonspecific agglutinating agents present in serum can be inactivated by well-known techniques which greatly reduce or eliminate the nonspecific agglutination observed at high concentration of serum.

Comparison of measurements of $\overline{D}$ performed on a dilution series of a sample of unknown antibody concentration with a standard curve of $\overline{D}$ vs C enables one to determine the unknown antibody titer. In fact, the absolute antibody concentration can be determined provided that the antibody in the known and unknown solutions have similar affinities for the antigen. To test the feasibility and accuracy of such a procedure for measuring antibody concentration, we repeated the assay procedure several times using different initial concentrations of antibody. Choosing the first of the $\overline{D}$ vs C curves as our standard curve, we could experimentally determine the initial concentration of antibody in the other samples. This determination was accomplished by (numerically) superimposing the 'unknown' $\overline{D}$ vs C on the standard curve. The standard deviation of the true antibody concentration from the experientally determined value was less than 10 percent of antibody concentration. We estimate that the preparation of the serial dilutions involved a 5 percent error. The automization of the preparation of antibody dilutions, the use of a dilution factor of less than two, and the experimental modifications mentioned above could further increase the accuracy of the method.

We claim:
1. The process for determining the concentration of a substance which promotes or inhibits an agglutination reaction which comprises:
   (a) determining the quantitative relationship between the mean diffusion constant of an agglutinated reaction product and the known concentration of the substance being tested using a fixed concentration of an agglutinant wherein the mean diffusion constant of the agglutinated reaction product is measured by quasi-elastic light scattering spectroscopy,
   (b) mixing an unknown concentration of one or more dilutions of the substance being tested with the same agglutinant to form at least one agglutinated reaction product of the dilutions,
   (c) determining the mean diffusion constant of the agglutinated reaction product of the dilutions by quasi-elastic light scattering spectroscopy and
   (d) comparing the mean diffusion constant of the agglutinated reaction product obtained in step (c) with the quantitative relationship determined by step (a).

2. The process of claim 1 wherein the agglutinant comprises antigen-coated carrier particles.

3. The process of claim 1 wherein the agglutinant comprises antibody-coated carrier particles.

4. The process of claim 1 wherein the substance being tested is an antigen which first is mixed with a fixed concentration of its complementary antibody and combining the resultant mixture with a fixed concentration of said antigen coated on carrier particles.

5. The process of claim 1 wherein the substance being tested is an antibody which first is mixed with a fixed concentration of its complementary antigen and combining the resultant mixture with a fixed concentration of said antibody coated on carrier particles.

6. The process of claim 1 wherein the substance being tested is an antigen which is combined with a fixed amount of its complementary antibody.

7. The process of claim 1 wherein the substance being tested is an antibody which is combined with a fixed amount of its complementary antigen.

8. The process of claim 4 wherein the antigen is luteinizing hormone.

9. The process of claim 4 wherein the antigen is human chorionic gonadotropin.

10. The process of claim 3 wherein the substance being tested is luteinizing hormone.

11. The process of claim 3 wherein the substance being tested is human chorionic gonadotropin.

12. The process of claim 6 wherein the antigen is luteinizing hormone.

13. The process of claim 6 wherein the antigen is human chorionic gonadotropin.

14. The process of claim 1 wherein the substance being tested is a virus and the agglutinant comprises red blood cells.

15. The process of claim 1 wherein the substance being tested comprises an antibody to a virus and wherein the agglutinated reaction products are obtained by mixing said antibody with a fixed concentration of said virus to inactivate said antibody and adding a fixed concentration of red blood cells to said mixture to effect an agglutination reaction of said virus and said blood cells.

16. The process of claim 1 wherein lymphocyte cells obtained from one individual are used to agglutinate the substance being tested which comprises lymphocyte cells obtained from a second individual.

* * * * *